United States Patent [19]
Johnson et al.

[11] Patent Number: 5,445,462
[45] Date of Patent: Aug. 29, 1995

[54] LIQUID APPLICATOR

[75] Inventors: Douglas P. Johnson, Leawood; A. Joseph Brandmeyer, Prairie Village, both of Kans.

[73] Assignee: Medi-Flex Hospital Products, Inc., Overland Park, Kans.

[21] Appl. No.: 228,737

[22] Filed: Apr. 18, 1994

Related U.S. Application Data

[63] Continuation-in-part of Ser. No. 101,581, Aug. 3, 1993, abandoned.

[51] Int. Cl.6 ............... A61M 35/00; A47L 13/17
[52] U.S. Cl. .................... 401/132; 401/133; 604/3
[58] Field of Search ............... 401/205, 132, 133; 604/3

[56] References Cited

U.S. PATENT DOCUMENTS

| | | |
|---|---|---|
| 2,642,065 | 5/1953 | Negri . |
| 2,977,014 | 3/1961 | Kock . |
| 3,152,352 | 10/1964 | Kosik, Jr. . |
| 3,369,543 | 2/1968 | Ronco . |
| 3,393,962 | 7/1968 | Andrews . |
| 3,614,245 | 10/1971 | Schwartzman . |
| 3,655,035 | 4/1972 | Muhlbauer . |
| 3,768,916 | 10/1973 | Avery . |
| 3,773,035 | 11/1973 | Aronoff et al. . |
| 3,792,699 | 2/1974 | Tobin et al. . |
| 3,891,331 | 6/1975 | Avery . |
| 3,918,435 | 11/1975 | Beall et al. . |
| 3,924,623 | 12/1975 | Avery . |
| 4,148,317 | 4/1979 | Meyer . |
| 4,183,684 | 1/1980 | Avery, Jr. . |
| 4,415,288 | 11/1983 | Gordon et al. . |
| 4,432,749 | 2/1984 | Snyder et al. . |
| 4,498,796 | 2/1985 | Gordon et al. . |
| 4,507,111 | 3/1985 | Gordon et al. . |
| 4,608,968 | 9/1986 | Rosofsky . |
| 4,747,719 | 5/1988 | Parkin . |
| 4,784,506 | 11/1988 | Koreska et al. . |
| 4,854,760 | 8/1989 | Pike et al. . |
| 4,875,602 | 10/1989 | Chickering et al. . |
| 4,925,327 | 5/1990 | Wirt . |
| 4,927,283 | 5/1990 | Fitjer . |
| 4,957,385 | 9/1990 | Weinstein . |
| 5,098,297 | 3/1992 | Chari et al. . |
| 5,152,742 | 10/1992 | Simpson . |
| 5,288,159 | 2/1994 | Wirt .................... 401/133 |
| 5,308,180 | 5/1994 | Pournoor et al. ......... 401/132 X |

FOREIGN PATENT DOCUMENTS 1021968  3/1966  United Kingdom ............ 401/132

*Primary Examiner*—Steven A. Bratlie
*Attorney, Agent, or Firm*—Hovey, Williams, Timmons & Collins

[57] ABSTRACT

A liquid applicator includes an elongated hollow body having opposed first and second open ends in fluid communication with one another, and a tip attached to the first open end and including a porous material. A closed, frangible ampul is supported within the second open end of the body and contains a liquid to be dispensed. A cap is provided at the second open end of the body, and which is movable axially relative to the body between a storage position and a use position in order to fracture the ampul. However, the cap is retained on the body and locked against movement from either of the storage or use positions toward the second open end of the body.

16 Claims, 3 Drawing Sheets

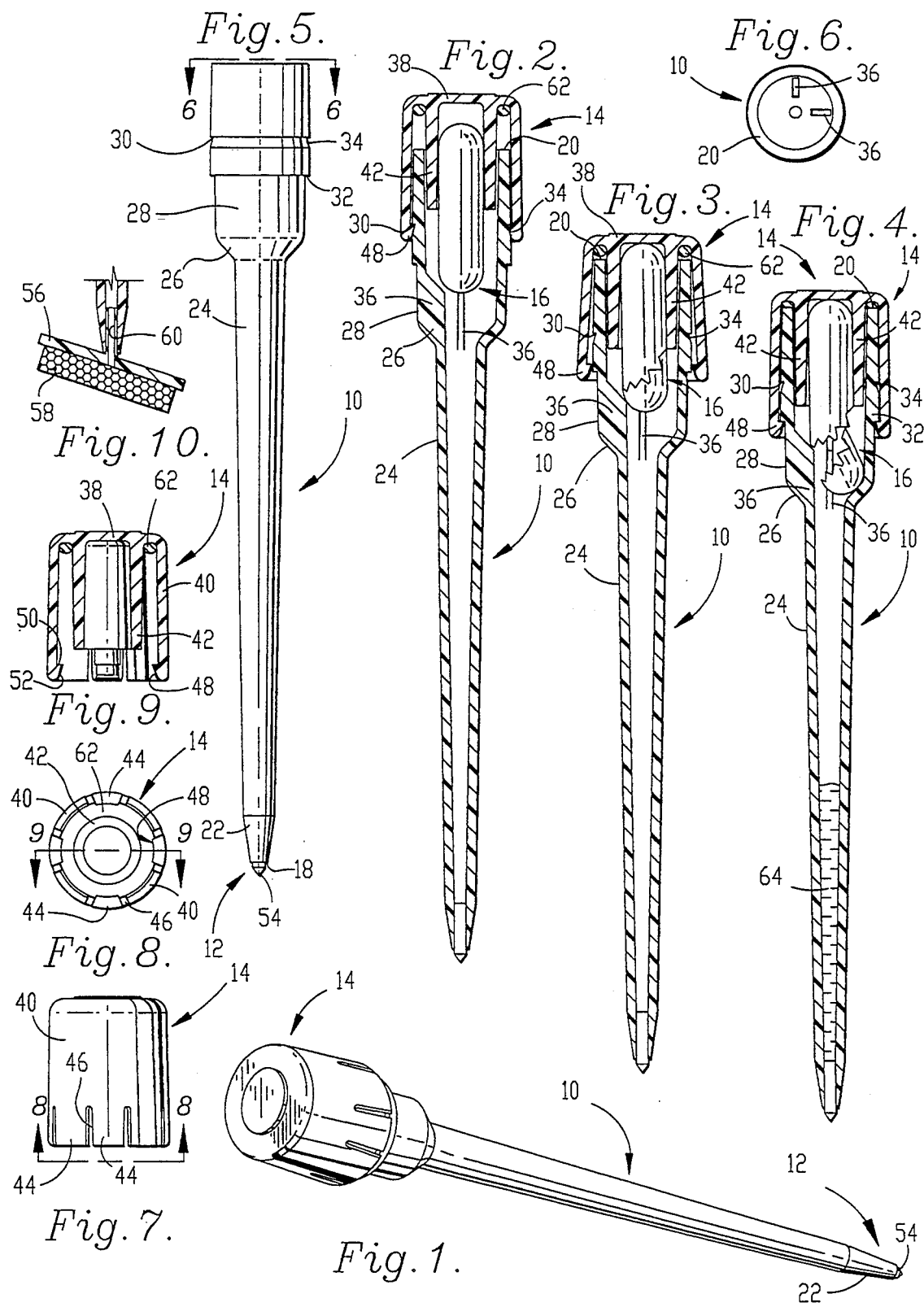

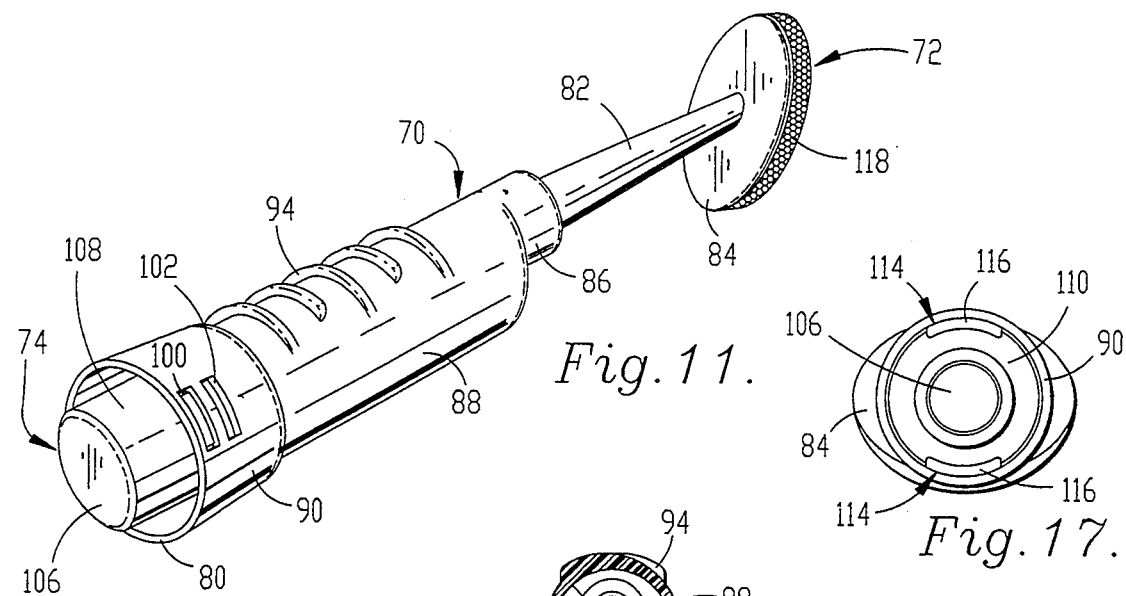
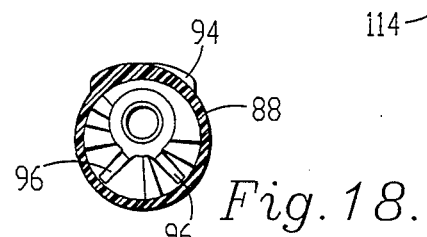
Fig. 17.
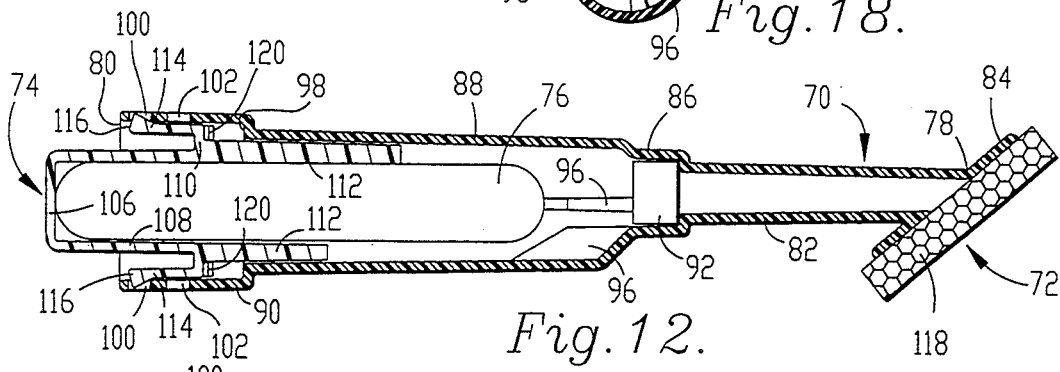
Fig. 18.
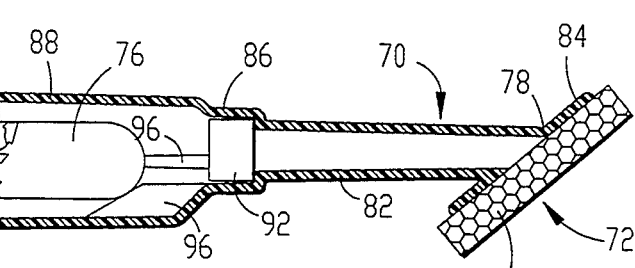
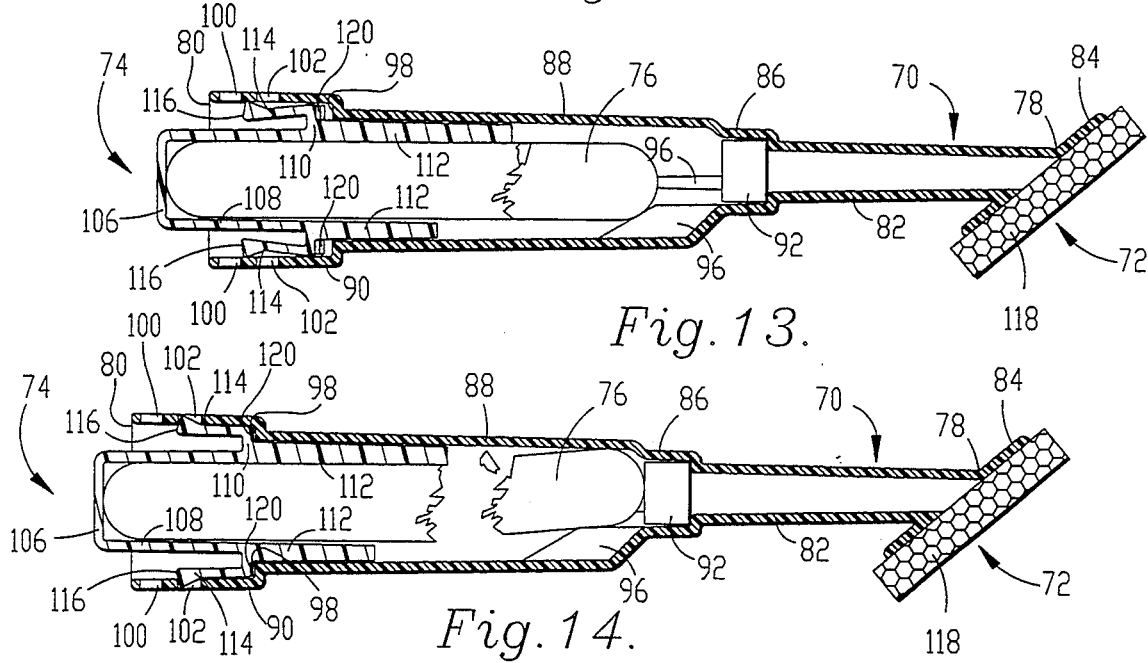

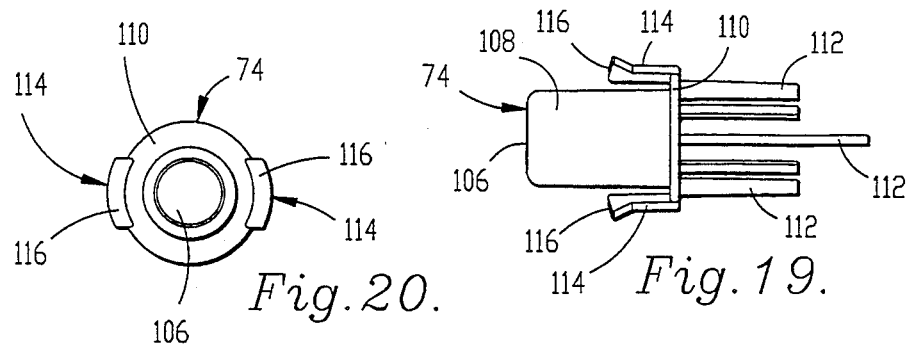
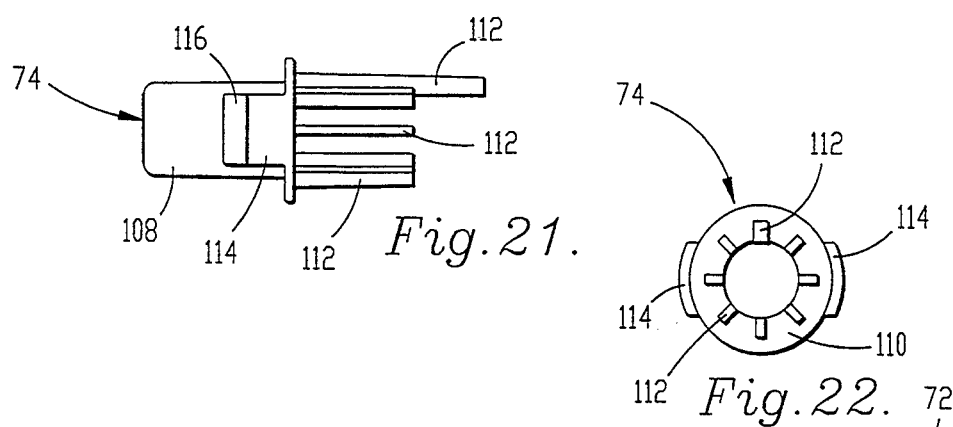
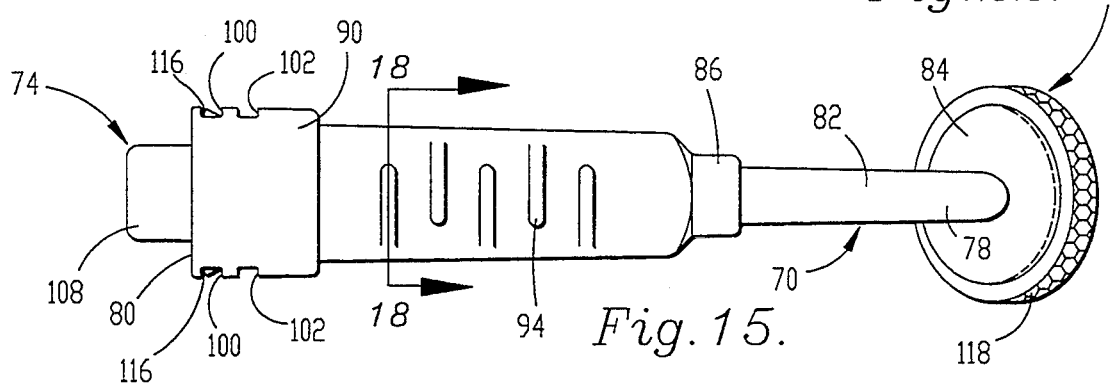
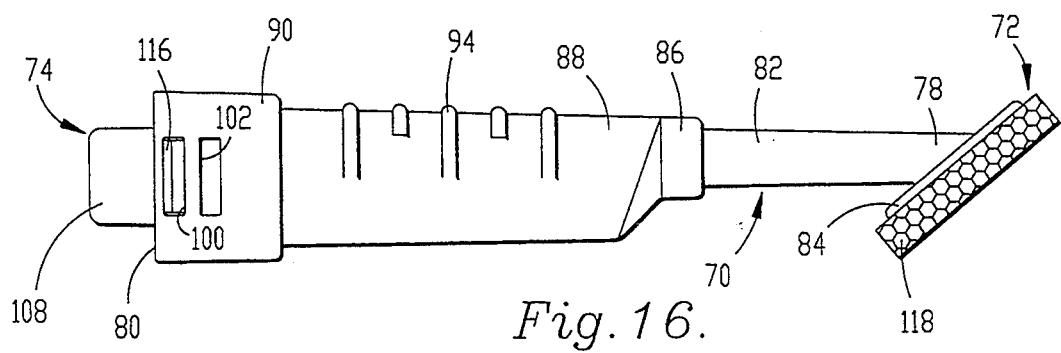

LIQUID APPLICATOR

RELATED APPLICATIONS

The present application is a continuation-in-part of U.S. Ser. No. 08/101,581, filed 3 Aug. 1993 now abandoned.

BACKGROUND OF THE INVENTION

1. Field of the Invention

The present invention relates generally to liquid applicators and, more particularly, to a disposable, self-contained applicator having an ampul in which liquid is stored, and a means for fracturing the ampul to release the liquid for application.

2. Discussion of the Prior Art

It is known to provide a liquid applicator of generally cylindrical construction, including a glass ampul retained within the applicator, a swab or tip exposed to the ampul, and a means for fracturing the ampul so that when the ampul is fractured, the liquid stored therein is dispensed to the swab for application.

However, numerous problems are encountered with devices of this type. For example, known devices include either an unnecessarily large number of moving parts, which renders such devices expensive to construct as a disposable assembly, or require that a user employ both hands in breaking the ampule and dispensing the fluid.

In many situations, it is necessary for the user of a fluid dispenser of antiseptics or medicaments to use one hand to expose or position the area of the body to be treated with the fluid while preparing the dispenser for use and applying the fluid with the other hand. Thus, it is very important for the user to be able to prepare and use the applicator with only one hand in order to enable the practical use thereof.

Another problem experienced with conventional applicators is that the pad used with many such applicators is useful only for applying a liquid over relatively large areas, without permitting a small volume of fluid to be accurately placed on a desired treatment location. It is known that where small amounts of fluid are to be applied at precise locations, a broken toothpick may be used in order to permit the fluid to be accurately placed without being inadvertently applied to surrounding areas.

An example of a particular use for an applicator capable of applying fluid to a very small treatment area exists in the treatment of exophytic genital and anal warts which are caused by certain types of HPV (human papillomaviruses), or which are strongly associated with genital dysplasia and carcinoma.

No therapy has been shown to eradicate HPV. Therefore, the goal of treatment is removal of exophytic warts and the amelioration of signs and symptoms, rather than the eradication of HPV.

Typically, treatment includes cryotherapy with liquid nitrogen. Cryoprobe is a treatment used for external genital and perianal warts. Other therapies include treatment with a variety of different fluids including but not limited to Podofilox or Podophyllotoxin (e.g. the product marketed under the trademark CONDYLOX, by Oclassen Pharmaceuticals, Inc.), silver nitrate, alcohol, TCA (trichloroacetic acid), podophyllin, or topical fluorouracil (e.g. the product marketed under the trademark EFUDEX).

As mentioned, it is known to use a toothpick or cotton-tipped swab to apply these treatments to a genital or perianal wart in an attempt to coat the wart without also applying the fluid to the surrounding skin. However, it is difficult to control the amount of fluid retained on a toothpick, and a swab does not permit accurate placement onto smaller warts without also coating the surrounding skin. Because many of the medications used cause severe irritation, such liberal application is undesirable.

OBJECTS AND SUMMARY OF THE INVENTION

It is an object of the present invention to provide a single-use, disposable liquid applicator which permits one-hand operation in order to free the second hand of the user for use in assisting with the applications of fluid to a desired area.

It is another object of the present invention to provide a liquid applicator which permits the accurate placement of a very small and closely controlled amount of liquid on a treatment area without also permitting the liquid to spread to surrounding areas.

Yet another object of the present invention resides in the provision of a liquid applicator which is easy to use and which enables a user to visually inspect the liquid within the applicator in order to determine the amount of liquid therein, and to control the flow of liquid from the applicator.

In accordance with these and other objects evident from the following description of a preferred embodiment of the invention, a liquid applicator includes an elongated hollow body having opposed first and second open ends in fluid communication with one another through the body, and a tip attached to the first open end of the body and including a porous material for permitting liquid within the body to be applied through the tip. A closed, frangible ampul is supported within the second open end of the body and contains a liquid to be dispensed. A cap is supported on the body at the second open end of the body, and is movable axially relative to the body between a storage position and a use position. A locking means is provided for retaining the cap on the body and locking the cap against movement from the use position toward the storage position.

The locking means of the liquid applicator includes a pair of axially spaced locking surfaces formed on the body adjacent the second open end, an engagement surface provided on the cap, and a biasing means for biasing the engagement surface toward the locking surfaces. The engagement surface is movable relative to the locking surfaces when the cap is moved toward the use position and engages the locking surfaces to lock the cap against movement from either of the storage or use positions in a direction toward the second open end of the body. A fracturing means fractures the ampul when the cap is moved from the storage position to the use position to permit the liquid in the ampul to flow through the body to the tip.

By constructing a liquid applicator in accordance with the present invention, numerous advantages are achieved. For example, by providing a relatively simple construction in which an ampule is stored within a body and is fractured at the time of use upon axial movement of a cap from the storage position to a use position, an applicator is obtained which may be designed for single use, and which enables one-handed operation.

Further, by providing the liquid applicator with a means for locking the cap against movement from the use position, it is possible to ensure that the applicator may not be reused after the fluid is emptied therefrom.

BRIEF DESCRIPTION OF THE DRAWING FIGURES

A preferred embodiment of the present invention is described in detail below with reference to the attached drawing figures, wherein:

FIG. 1 is a perspective view of a first liquid applicator constructed in accordance with the preferred embodiment;

FIG. 2 is a sectional side view of the first applicator, illustrating the applicator in a storage position;

FIG. 3 is a sectional side view of the first applicator, illustrating the applicator during movement of a cap of the applicator from the storage position toward a use position;

FIG. 4 is a sectional side view of the first applicator, illustrating the applicator in the use position;

FIG. 5 is a side elevational view of a body of the first applicator;

FIG. 6 is a top plan view of the body;

FIG. 7 is a side elevational view of the cap;

FIG. 8 is a bottom plan view of the cap;

FIG. 9 is a sectional view of the cap taken along line 9—9 of FIG. 8;

FIG. 10 is a fragmentary sectional view of the first applicator, illustrating an alternate construction of a tip employed with the applicator;

FIG. 11 is a perspective view of a second liquid applicator constructed in accordance with the preferred embodiment;

FIG. 12 is a sectional side view of the second applicator, illustrating the applicator in a storage position;

FIG. 13 is a sectional side view of the second applicator, illustrating the applicator during movement of a cap of the applicator from the storage position to a use position;

FIG. 14 is a sectional side view of the second applicator, illustrating the applicator in the use position;

FIG. 15 is a front elevational view of a body of the second applicator;

FIG. 16 is a side elevational view of the second applicator;

FIG. 17 is a top plan view of the second applicator;

FIG. 18 is a sectional view taken along line 18—18 of FIG. 15;

FIG. 19 is a front elevational view of the cap;

FIG. 20 is a top plan view of the cap;

FIG. 21 is a side elevational view of the cap; and

FIG. 22 is a bottom plan view of the cap.

DETAILED DESCRIPTION OF THE PREFERRED EMBODIMENT

A first liquid applicator constructed in accordance with a preferred embodiment of the present invention is illustrated in FIGS. 1–9, and generally includes an elongated body 10, a tip 12 attached to one end of the body, and a cap 14 supported on an opposing end of the body. As shown in FIG. 2, the applicator also includes a closed, frangible ampul 16 supported within the end of the body adjacent the cap and containing a liquid to be dispensed.

The elongated body 10 is of generally hollow cylindrical shape, including a first open end 18 and a second open end 20, the ends being in fluid communication with one another through the body. The body is preferably formed of a translucent material which permits inspection of the liquid within the body during use.

Preferably, the first open end 18 of the body is tapered toward the tip 12 to present a gripping region 22 by which the applicator may be handled by a user. This gripping region resembles a writing pen in design so that the user may manipulate the applicator comfortably in order to accurately apply fluid to a particular, small area without inadvertently dispensing fluid to surrounding areas.

The intermediate portion 24 of the body is preferably continuously tapered outward toward the second end, and includes a stepped region 26 defining an enlarged end section 28 adjacent the second open end 20. As shown in FIG. 5, the exterior surface of the body along the enlarged end section includes a pair of axially spaced ridges 30, 32 and a ramp 34 extending between the ridges.

Returning to FIG. 2, a pair of protuberances or fins 36 are formed within the interior of the enlarged end section of the body and extend radially into the second open end of the body by a distance sufficient to interfere with free movement of the ampul within the enlarged end section 28. The fins 36 extend axially toward the second open end of the body from the stepped region 26 and are spaced axially from the ampul during storage of the applicator, as described more fully below. As shown in FIG. 6, the fins are offset from one another by about 90° relative to the longitudinal axis of the body.

The cap 14 is illustrated in FIG. 9, and includes a circular end wall 38 and a tubular side wall 40 having a first end connected to the end wall and a second free end. The side wall 40 is of a diameter sized for receipt over the second open end 20 of the body. The cap also includes an ampul receiving means for supporting the ampul within the body of the applicator. This ampul receiving means preferably includes an inner tubular sleeve 42 connected to the end wall 38 and extending toward the free end of the side wall. The inner sleeve 42 is sized for receipt within the second open end of the body such that the second open end is received between the inner sleeve and the side wall of the cap when the cap is positioned on the body, as shown in FIG. 2.

As shown in FIG. 7, the cap 14 includes a plurality of axially extending tabs 44 at the free end of the tubular side wall, the tabs being separated from one another by axial slots 46 formed in the cap. Turning to FIG. 8, four of the tabs include teeth 48 which are directed radially inward of the side wall toward the inner tubular sleeve of the cap. The teeth 48 are shown in FIG. 9 to include a flat inner end surface 50 and a ramp 52 extending between the surface 50 and the free end of the side wall.

A preferred tip 12 is shown in FIG. 2, and includes an elongated piece of porous material for permitting liquid within the body to be applied through the tip. Preferably, the material used in the tip is similar to conventional materials used in felt tip markers or the like, and is directly received within the first open end of the body without the need for additional mounting expedients. The tip includes a tapered end 54 extending from the body, and may be sculpted by a user, with the use of scissors, a knife or the like, to present any desired tip configuration.

An alternate embodiment of the tip is shown in FIG. 10, and includes a tip support 56 retained within the first open end of the body and a pad 58 of porous material secured to the support. Preferably, the support includes a conduit for providing fluid communication between the pad and the hollow interior of the body. A desired shape of the pad 58 is circular in order to permit this applicator to be used in applying antiseptic solutions over large areas to be cleaned or prepared for medical operations.

The first liquid applicator is illustrated in a storage position in FIG. 2. The ampul 16 is received within the inner tubular sleeve 42 of the cap 14, and the cap is fitted over the second open end 20 of the body 10 with the sleeve received within the enlarged end section of the body and the side wall encircling the second open end. In this manner, the cap covers and closes the second open end of the body, while the tip 12 closes the first open end 18.

In this position, the teeth 48 of the cap engage the ridge 30 provided on the outer surface of the body, and engagement between the end surfaces of the teeth with the ridge prevent the cap from being removed from the body. Thus, once assembled, the applicator is locked against disassembly. During storage, the ampul 16 provides a hermetically sealed container within which any desired fluid may be stored without degradation for relatively long periods of time.

Prior to use of the applicator, the user pushes the cap 14 axially along the body from the storage position, shown in FIG. 2, toward a final use position shown in FIG. 4. During this movement, as shown in FIG. 3, the tabs carrying the teeth 48 are biased radially outward by the ramp 34 extending between the ridges. The side wall of the cap is formed of a material having sufficient resilience to permit this radial movement of the tabs and to provide a biasing force which continuously urges the tabs radially inward.

As the cap moves from the storage to the use position, the axially inner end of the ampul is brought into engagement with the fins 36 and is compressed between the fins and the end wall 38 of the cap. At the time of this axial compression of the ampul, the fins also exert a lateral pressure on the axially inner end of the ampul. This lateral pressure is balanced by an equal and opposite pressure exerted by the free end of the inner tubular sleeve 42 located intermediate the ends of the ampul, and causes the ampul to fracture.

As the cap reaches the use position, as illustrated in FIG. 4, the teeth 48 engage the ridge 32 of the body, locking the cap in the use position and preventing the cap from being moved back toward the storage position. A resilient O-ring 62, formed of rubber or the like, is received within the cap between the inner tubular sleeve and the side wall such that, when the cap is moved to the use position, the seal 62 is compressed between the end wall of the cap and the edge of the second open end of the body. The O-ring provides a fluid-tight seal between the cap and the body when the cap is in the use position so that fluid released from the ampul cannot leak from the second open end.

After the ampul has been fractured, the fluid 64 contained therein is released and is free to flow throughout the interior of the body. If the applicator is tipped into a vertical orientation as shown in FIG. 4, the fluid flows to the tip and is absorbed by the tip. Thereafter, application of the fluid is accomplished by touching the tip to the desired area.

If it is desired to apply a liberal amount of fluid to a precise point, the user can simply squeeze the body, which is preferably formed of a resilient material such as thin-walled plastic material or the like, and fluid is pressured through the tip onto the application point.

The entire process of moving the cap to the use position and applying liquid to a desired point is achieved with the use of only one hand of the user, who simply has to carry out the necessary movement of the cap with their thumb while holding the body of the container between their fingers. Thus, operation of the applicator is similar to that of a retractable pen, with which most users are already accustomed. Further, where the alternate construction of the tip is employed on the applicator, the operation is identical and also permits one-handed operation.

A second liquid applicator constructed in accordance with the preferred embodiment of the invention is illustrated in FIG. 11, and generally includes an elongated body 70, a tip 72 attached to one end of the body, and a cap 74 supported within an opposing end of the body. As shown in FIG. 12, the applicator also includes a closed, frangible ampul 76 supported within the end of the body adjacent the cap and containing a liquid to be dispensed.

The second applicator is similar to the first applicator in that it permits single-handed operation during fracturing of the ampul and application of the fluid. However, the second applicator employs a large tip useful in applying greater amounts of fluid, e.g. antiseptic solutions, over areas to be prepared for medical operations. In addition, the body of the second applicator is sized to receive an ampul large enough to contain fluid for a single use of the applicator.

The elongated body 70 is of generally hollow cylindrical shape, including a first open end 78 and a second open end 80, the ends being in fluid communication with one another through the body. The body is preferably formed of a translucent material which permits inspection of the liquid within the body during use.

Preferably, as shown in FIG. 11, the body includes a tapered region 82 adjacent the first open end of the body, and an annular rim 84 surrounding the first open end. The rim is angled relative to the longitudinal axis of the body, and defines a support surface on which the tip 72 is secured. The angle of the rim is chosen to enable a user to apply liquid to a generally horizontal surface while holding the body of the applicator at an angle of about 45° relative to the surface.

As shown in FIG. 16, the diameter of the body increases between the tapered region 82 and the second open end 80 of the body in a stepwise fashion, and includes three stepped regions 86, 88, 90. The first region 86 adjacent the tapered region is generally cylindrical, but is offset from the longitudinal axis of the body. As shown in FIG. 12, this first region 86 defines a seat for receiving a porous wall 92.

Returning to FIG. 16, the second stepped region 88 is cylindrical, and includes several external circumferential ridges 94 adapted to facilitate handling of the applicator. Internally, as shown in FIG. 12, the second stepped region includes a pair of protuberances or fins 96 which extend radially into the body by a distance sufficient to interfere with free movement of the ampul within the body. The fins 96 extend axially toward the second open end of the body from the first stepped region 86 and are spaced axially from the ampul during storage of the applicator. As shown in FIG. 18, the fins are offset from one another by about 90° relative to the longitudinal axis of the body.

The outer stepped region 90 of the body is illustrated in FIG. 15, and is of an enlarged diameter relative to the other stepped regions 86, 88. As shown in FIG. 12, the transition between the second and third regions defines a shelf 98 facing the second open end of the body. This shelf 98 defines a stop against which the cap 74 abuts when the cap is moved into the body to the use position, and prevents the cap from being forced beyond the use position.

The inner surface of the outer region of the body includes a pair of slots 100, 102 on each side of the second open end, wherein each pair of slots presents axially spaced locking surfaces. The slots 100, 102 extend in the circumferential direction of the body, and may either extend completely through the body, as illustrated, or partially radially outward from the inner surface.

The cap is illustrated in FIG. 11, and includes a circular end wall 106 and a tubular side wall 108 having a first end connected to the end wall and a second free end. As shown in FIG. 21, the cap includes an annular flange 110 adjacent the free end of the side wall. The flange is sized for receipt within the outer stepped region 90 of the body, as shown in FIG. 17, and is adapted to seat against the shelf 98 of the body to seal the applicator against leakage during use, as shown in FIG. 14.

Turning to FIG. 19, a plurality of fingers 112 extend axially from the free end of the cap 74 and define an ampul receiving means for supporting the ampul within the body of the applicator. As shown in FIG. 12, the cap is hollow so that when an ampul is placed in the cap, the ampul extends from the end wall 106 past the ends of the fingers 112. In this manner, the ampul is supported within the body against unwanted movement in a direction transverse to the longitudinal axis of the body. As shown in FIG. 22, the fingers and side wall of the cap are of the same inner diameter, which is substantially equal to the outer diameter of the ampul so that the ampul nests in the cap.

As shown in FIG. 19, the cap includes a pair of axially extending tabs 114 at the free end of the tubular side wall, the tabs being secured to the outer edge of the annular flange 110 and extending toward the end wall 106. Each tab includes a resilient arm presenting a free end on which an engagement surface 116 is defined. These engagement surfaces are illustrated in FIG. 20. Preferably, the engagement surfaces are either flat or angled slightly relative to a plane extending in a direction transverse to the longitudinal axis of the body, as shown in FIG. 12, so that the engagement surfaces 116 of the arms will lock in the slots 100, 102 to prevent movement of the cap in a direction toward the second open end of the body from either the storage or use position. However, the outer circumferential surface of each arm is ramped between the flange and the free end to facilitate movement of the cap in a direction toward the use position.

A preferred tip 72 is shown in FIG. 12, and includes a porous circular pad 118 which permits the applicator to be used in applying antiseptic solutions over large areas to be cleaned or prepared for medical operations. The tip 72 is secured to the rim 84 of the body by any suitable means, such as by an adhesive or the like.

The second liquid applicator is illustrated in a storage position in FIG. 12. The ampul 76 is received within the cap 74, and the cap is fitted into the second open end of the body 70. In this position, the engagement surfaces 116 of the cap tabs 114 engage the axially outer slots 100 provided on the inner surface of the body to lock the cap against removal from the body. Thus, once assembled, the applicator is locked against disassembly.

During storage, the ampul 76 provides a hermetically sealed container within which any desired fluid may be stored without degradation for relatively long periods of time. Prior to use of the applicator, the user pushes the cap axially along the body from the storage position toward a final use position shown in FIG. 14. During this movement, as shown in FIG. 13, the tabs 114 are biased radially inward by the ramped circumferential surfaces of the arms bearing against the inner surface of the body. The tabs are formed of a material having sufficient resilience to permit this radial movement to provide a biasing force which continuously urges the arms radially outward.

As the cap moves from the storage to the use position, the axially inner end of the ampul is brought into engagement with the fins 96 and is compressed between the fins and the end wall 106 of the cap. At the time of this axial compression of the ampul, the fins also exert a lateral pressure on the axially inner end of the ampul. This lateral pressure is balanced by an equal and opposite pressure exerted by the fingers 112 of the cap, and causes the ampul to fracture.

As the cap reaches the use position, as illustrated in FIG. 14, the engagement surfaces 116 engage the axially inner slots 102 of the body, locking the cap in the use position against movement back toward the storage position. A resilient O-ring 120, formed of rubber or the like, may be provided between the flange of the cap and the shelf of the body such that, when the cap is moved to the use position, the seal is compressed between the flange and the shelf to provide a fluid-tight seal between the cap and the body.

After the ampul has been fractured, the fluid contained therein is released and is free to flow throughout the interior of the body. The porous wall 92 allows fluid to flow to the tip, while retaining the fractured ampul within the second stepped region 88 of the body. If it is desired to apply a liberal amount of fluid over a large surface area, the user can simply squeeze the body, which is preferably formed of a resilient material such as thin-walled plastic or the like, and fluid is pressured through the tip onto the application area.

Although the invention has been described with reference to the preferred embodiment illustrated in the attached drawing figures, it is noted that substitutions may be made and equivalents employed herein without departing from the scope of the invention as recited in the claims.

What is claimed is:

1. A liquid applicator comprising:
   an elongated hollow body having opposed first and second open ends in fluid communication with one another through the body;
   a tip attached to the first open end of the body and including a porous material for permitting liquid within the body to be applied through the tip;
   a closed, frangible ampul supported within the second open end of the body and containing a liquid to be dispensed;
   a cap supported on the body at the second open end of the body, the cap being movable axially relative to the body between a storage position and a use position;
   a locking means for retaining the cap on the body and locking the cap against movement from either of the storage or use positions in a direction toward the second open end of the body, the locking means including a pair of axially spaced locking surfaces formed on the body adjacent the second open end, an engagement surface provided on the cap, and a biasing means for biasing the engagement surface toward the locking surfaces, the engagement surface being movable relative to the locking surfaces when the cap is moved toward the use position and engaging the locking surfaces to lock the cap against movement from either of the storage or use positions in a direction toward the second open end of the body; and a fracturing means for fracturing the ampul when the cap is moved from the storage position to the use position to permit the liquid in the ampul to flow through the body to the tip.

2. A liquid applicator as recited in claim 1, wherein the body is tubular, and is tapered toward the first open end and enlarged adjacent the second open end.

3. A liquid applicator as recited in claim 1, wherein the body is formed of a translucent material which permits inspection of the liquid within the body.

4. A liquid applicator as recited in claim 1, wherein the porous material of the tip is attached directly to the first open end of the body.

5. A liquid applicator as recited in claim 1, wherein the tip includes a support means for supporting the tip on the body, the support means having a passage for providing fluid communication between the first open end and the porous material of the tip.

6. A liquid applicator as recited in claim 1, wherein the tip is tapered to a point for permitting accurate application of a small amount of liquid.

7. A liquid applicator as recited in claim 1, wherein the ampul is formed of glass.

8. A liquid applicator as recited in claim 1, wherein the cap includes an ampul receiving means for supporting the ampul within the body.

9. A liquid applicator as recited in claim 8, wherein the body includes an enlarged diameter section adjacent the second open end which defines an annular shelf facing the second open end, and the cap includes a circular end wall, a tubular side wall having a first end connected to the end wall and a second free end, and an annular flange intermediate the ends of the side wall, the annular flange being sized for receipt within the enlarged diameter section of the body.

10. A liquid applicator as recited in claim 9, further comprising sealing means for providing a seal between the cap and the body when the cap is in the use position.

11. A liquid applicator as recited in claim 10, wherein the sealing means includes an o-ring supported in the enlarged diameter section of the body adjacent the annular shelf so that, when the cap is moved to the use position, the o-ring is compressed between the annular flange of the cap and the annular shelf of the body to provide a liquid tight seal.

12. A liquid applicator as recited in claim 1, further comprising a porous wall means positioned between the ampul and the first open end of the body for retaining the fractured ampul within the body and for facilitating the flow of liquid to the tip.

13. A liquid applicator as recited in claim 1, wherein the fracturing means includes a protuberance extending into the second open end of the body and being offset from the ampul by a distance less than the distance of travel of the cap when the cap is moved from the storage position to the use position so that movement of the cap brings the ampul and protuberance into engagement with one another fracturing the ampul.

14. A liquid applicator as recited in claim 9, wherein the fracturing means includes a protuberance provided on the body, the protuberance extending radially into the second open end of the body and being offset axially from the ampul by a distance less than the distance of travel of the cap when the cap is moved from the storage position to the use position so that movement of the cap to the use position brings the ampul against the protuberance fracturing the ampul.

15. A liquid applicator as recited in claim 13, wherein the fracturing means includes two protuberances, each of which are offset from one another by about 90° relative to the longitudinal axis of the body.

16. A liquid applicator comprising:

an elongated hollow body having opposed first and second open ends in fluid communication with one another through the body and a cylindrical region intermediate the ends;

a tip attached to the first open end of the body and including a porous material for permitting liquid within the body to be applied through the tip;

a closed, frangible ampul supported within the cylindrical region of the body and containing a liquid to be dispensed, the ampul having an outer diameter smaller than the inner diameter defined by the cylindrical region of the body;

a hollow cap supported on the body at the second open end of the body, the cap being movable axially relative to the body between a storage position and a use position, and including a tubular side wall having an outer diameter substantially equal to the inner diameter defined by the cylindrical region of the body and an inner diameter substantially equal to the outer diameter of the ampul, the side wall defining a receiving means for supporting the ampul within the cylindrical region of the body;

a locking means for retaining the cap on the body and locking the cap against movement from either of the storage or use positions in a direction toward the second open end of the body, the locking means including a pair of axially spaced locking surfaces formed on the body adjacent the second open end, an engagement surface provided on the cap, and a biasing means for biasing the engagement surface toward the locking surfaces, the engagement surface being movable relative to the locking surfaces when the cap is moved toward the use position and engaging the locking surfaces to lock the cap against movement from either of the storage or use positions in a direction toward the second open end of the body; and a fracturing means for fracturing the ampul when the cap is moved from the storage position to the use position to permit the liquid in the ampul to flow through the body to the tip.

* * * * *